United States Patent [19]

Steinberg et al.

[11] Patent Number: 5,198,134
[45] Date of Patent: Mar. 30, 1993

[54] SUBSTITUTED NAPHTHALENEDIAMINE STABILIZERS

[75] Inventors: David H. Steinberg, Bronx; John J. Luzzi, Carmel, both of N.Y.

[73] Assignee: Ciba-Geigy Corporation, Ardsley, N.Y.

[21] Appl. No.: 783,953

[22] Filed: Oct. 28, 1991

Related U.S. Application Data

[63] Continuation-in-part of Ser. No. 696,694, May 7, 1991, abandoned.

[51] Int. Cl.$^5$ ............... C10M 105/64; C07C 211/58
[52] U.S. Cl. ........................ 252/50; 252/47; 564/308; 564/340; 564/428
[58] Field of Search ............ 252/50, 47; 564/308, 564/340, 428

[56] References Cited

U.S. PATENT DOCUMENTS

| | | | |
|---|---|---|---|
| 2,004,526 | 6/1935 | Graseby | 194/239 |
| 2,070,521 | 2/1937 | Calvert | 564/428 |
| 3,336,386 | 8/1967 | Dovell et al. | 252/401 |
| 3,406,202 | 10/1968 | Reifschneider | 564/428 |
| 3,509,214 | 4/1970 | Braid et al. | 564/308 |
| 3,535,243 | 10/1970 | Chao | 252/51.5 A |
| 3,573,206 | 3/1971 | Braid et al. | 252/401 |
| 5,068,435 | 11/1991 | Burgoyne, Jr. | 564/308 |

OTHER PUBLICATIONS

Ind. Eng. Chem. Prod. Res. Dev. 1984, 23, pp. 21–27.
P. Iwa et al., J. Phys. Chem. 86, 1277 (1982).
R. Gleiter et al., J. Org. Chem. 51, 370 (1986).
J. Chem. Soc., Perkin Trans., 1, 2849.
Chem. Abst. 102, 6382x (1985).
Chem. Abst. 103, 125225d (1985).
A. F. Pozharskii et al., Zh. Org. Khim. 17, 1005 (1981).
A. F. Pozharskii et al., Zh. Org. Khim. 20, 1567 (1984).

*Primary Examiner*—Prince Willis, Jr.
*Assistant Examiner*—Thomas Steinberg
*Attorney, Agent, or Firm*—Luther A. R. Hall

[57] ABSTRACT

N-Allyl and N-methylene-thio substituted naphthalene-1,8- or -1,5-diamine compounds are very effective antioxidant stabilizers for organic material subject to oxidative or thermal degradation, particularly for lubricant compositions.

15 Claims, No Drawings

SUBSTITUTED NAPHTHALENEDIAMINE STABILIZERS

This is a continuation-in-part of application Ser. No. 696,694, filed on May 7, 1991 now abandoned.

This invention pertains to N-allyl and N-methylenethio substituted naphthalene-1,8-or -1,5-diamines and their use as antioxidant stabilizers for lubricant compositions.

BACKGROUND OF THE INVENTION

The use of aromatic amines as stabilizers for lubricant compositions is well-known in the art. U.S. Pat. Nos. 3,509,214 and 3,573,206 typify the state of the art for such products.

It is well-known that many organic liquids and solids used in industrial applications, such as oils and greases, power transmission fluids, resin and polymer coatings, insulations, structural products and the like, may deteriorate when subjected to oxidation. Since these substances are very often used at high temperatures, the rate of oxidative breakdown can be very rapid. This problem is particularly important in the operation of modern day automotive and aircraft engines. The breakdown of the lubricating oil, either natural or synthetic, is frequently accompanied by the formation of corrosive acids, sludge and other breakdown products. These resulting products can harm the metal surfaces of the engine and interfere with the efficient operation of the lubricants.

U.S. Pat. Nos. 3,509,214 and 3,573,206 disclose that the stability of the organic compounds used in such lubricants which are normally susceptible to oxidative deterioration could be unexpectedly improved by the addition thereto of an N-arylnaphthylamine containing lower oligomer obtained by subjecting said N-arylnaphthylamine or mixture of said N-arylnaphthylamine with a diphenylamine or a second N-arylnaphthylamine to either thermal or chemical oxidation or both.

U.S. Pat. No. 3,336,386 describes N,N'-diisopropyl-1,5-naphthalenediamine and related dialkylated derivatives as being useful antioxidant stabilizers for elastomers.

U.S. Pat. No. 3,535,243 describes lubricant additives which are inter alia N-alkylated diaminonaphthalenes, but this reference specifically teaches away from the presence of unsaturated substituents on such molecules. U.S. Pat. No. 2,070,521 discloses various dialkylnaphthylamines as antioxidants, but there is no mention of naphthalenediamine derivatives. U.S. Pat. No. 3,406,202 describes N-alkenyl substituted naphthylamines, but there is no mention of naphthalenediamine derivatives. Additionally, the compounds of this patent must also be substituted on the aromatic ring by a —SR group which is not present in the instant compounds. U.S. Pat. No. 2,004,526 teaches N-aryl substituted naphthalenediamines as antioxidants, but these are compounds clearly outside the scope of the instant invention.

A number of N-alkyl substituted 1,8- or 1,5-naphthalenediamine compounds are known in the prior art as seen below:

J. Phys. Chem. 86, 1277 (1982) describes N,N,N',N'-tetramethyl-1,5-naphthalenediamine;

J. Org. Chem. 51, 370 (1986) describes N,N'-dimethyl-1,8-naphthalenediamine;

J. Chem. Soc., Perkin Trans. 1, 2840 describes N,N,N',N'-tetra alkylated 1,8-naphthalenediamines;

Zh. Org. Khim. 17, 1005 (1981); Chem. Abst. 95, 187185r describes the general synthetic methods used to prepare di-, tri- and tetra-N-substituted 1,8-naphthalenediamines;

Zh. Org. Khim. 20, 1567 (1984); Chem. Abst. 102, 6382x (1985) describes N-ethyl-1,8-naphthalenediamine;

Ind. Eng. Chem., Prod. Res. Dev. 23, 21 (1984) describes N-octyl-1,5-naphthalenediamine and N-octadecyl-1,8-naphthalenediamine as antioxidants for lubricants;

ACS Div. Petroleum Chem. 27, 362 describes N-octyl- and N-octadecyl-1,8-naphthalenediamine; and Japanese Sho 60-81268 (=Chem. Abst. 103, 125225d (1985) describes N,N'-didodecyl-1,8-naphthalenediamine.

The instant invention pertains to N-alkenylated, preferably N-allylated, naphthalenediamines and N-methylene-thio substituted naphthalenediamines which have been found to have superior antioxidant properties in lubricant compositions.

OBJECTS OF THE INVENTION

One object of the invention is to provide new N-alkenylated or N-methylene-thio substituted naphthalenediamine compounds which are effective antioxidants for lubricant compositions.

Another object of this invention is to provide organic lubricant compositions having improved oxidation or thermal stability using an effective amount of an N-alkenylated or N-methylene-thio substituted naphthalenediamine.

DETAILED DISCLOSURE

The instant invention pertains to an N-substituted 1,5- or 1,8-naphthalenediamine of formula I or II

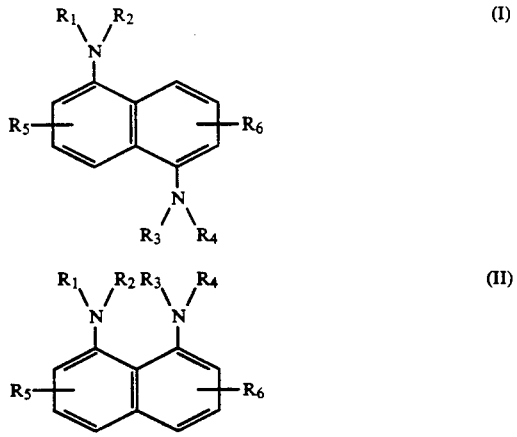

wherein $R_1$, $R_2$, $R_3$ and $R_4$ are independently hydrogen, alkenyl of 3 to 18 carbon atoms or —CH$_2$—S—E$_1$, —CH$_2$—S—C$_n$H$_{2n}$—S—E$_1$ or —CH$_2$—S—T—COO—E$_2$ where n is 2 to 6, E$_1$ is alkyl of 1 to 18 carbon atoms, alkenyl of 3 to 18 carbon atoms, cycloalkyl of 5 to 12 carbon atoms, phenylalkyl of 7 to 9 carbon atoms, aryl of 6 to 10 carbon atoms, or said aryl or said phenylalkyl substituted on the aryl or phenyl moiety by one or two alkyl of 1 to 8 carbon atoms or by hydroxy and by one or two alkyl of 1 to 8 carbon atoms, E$_2$ is alkyl of 1 to 18 carbon atoms, alkenyl of 3 to 18 carbon atoms, cycloalkyl of 5 to 12 carbon atoms, aryl of 6 to 10 carbon atoms or phenylalkyl of 7 to 9 carbon atoms, and T is methylene, ethylene or ethylidene, with the proviso that all of $R_1$, $R_2$, $R_3$ and $R_4$ are not hydrogen at the same time, and with the further proviso that in formula II, none of $R_1$, $R_2$, $R_3$ and $R_4$ is —$CH_2S$—$E_1$, —$CH_2$—$S$—$C_nH_{2n}$—$S$—$E_1$ or —$CH_2$—$S$—$COO$—$E_2$, and $R_5$ and $R_6$ are independently hydrogen, alkyl of 1 to 12 carbon atoms, alkenyl of 3 to 18 carbon atoms, cycloalkyl of 5 to 12 carbon atoms, phenylalkyl of 7 to 15 carbon atoms or aryl of 6 to 10 carbon atoms.

Preferably $R_1$, $R_2$, $R_3$ and $R_4$ are independently hydrogen, allyl, methallyl, —$CH_2$—$S$—$E_1$, —$CH_2$—$S$—$C_nH_{2n}$—$S$—$E_1$ or —$CH_2$—$S$—$T$—$COO$—$E_2$ where n is 2, $E_1$ or $E_2$ is alkyl of 2 to 12 carbon atoms, and T is methylene, with the proviso that at least two of $R_1$, $R_2$, $R_3$ and $R_4$ are not hydrogen.

Most preferably $R_1$, $R_2$, $R_3$ and $R_4$ are independently hydrogen, allyl, methallyl, —$CH_2$—$S$—$E_1$ or —$CH_2$—$S$—$T$—$COO$—$E_2$ where $E_1$ or $E_2$ is alkyl of 8 to 12 carbon atoms, T is methylene and at least two of $R_1$, $R_2$, $R_3$ and $R_4$ are not hydrogen. Especially preferred at least one of $R_1$, $R_2$, $R_3$ and $R_4$ is allyl.

Preferably $R_5$ and $R_6$ are independently hydrogen or alkyl of 1 to 4 carbon atoms; most preferably hydrogen.

The N-alkenyl substituted compounds of this invention are conveniently prepared by reaction of 1,5- or 1,8-naphthalenediamine with an alkenyl halide, such as allyl bromide or methallyl chloride, in the presence of alkali and a quaternary alkylammonium salt. These intermediates are largely items of commerce.

The instant compounds substituted on the N-atom by —$CH_2$—$S$—$E_1$, —$CH_2$—$S$—$C_nH_{2n}$—$S$—$E$ or by —$CH_2$—$S$—$T$—$COO$—$E_2$ are prepared by a Mannich reaction using the 1,5-naphthalenediamine, formaldehyde and mercaptan or an ester of a mercaptoalkanoic acid, such as a mercaptoacetic, mercaptolactic or 3-mercaptopropionic acid ester. These materials too are largely items of commerce.

When any of $R_1$ to $R_6$ or $E_1$ or $E_2$ is alkyl, such alkyl groups are, for example, methyl, ethyl, isopropyl, n-butyl, tert-butyl, tert-amyl, 2-ethylhexyl, n-octyl, lauryl or n-octadecyl; when said radicals are alkenyl, they are for example, allyl, methallyl and oleyl; when said radicals are cycloalkyl, they are, for example cyclopentyl, cyclohexyl, cyclooctyl and cyclododecyl; when said radicals are phenylalkyl, they are, for example, benzyl, phenethyl, α-methylbenzyl and α,α-dimethylbenzyl; when said radicals are aryl, they are, for example phenyl or naphthyl.

The instant invention also relates to lubricant compositions, having improved oxidation or thermal stability, which comprises (a) a major amount of a lubricant, subject to oxidative or thermal degradation, and (b) an effective stabilizing amount of a compound of formula I or II as described above.

The lubricant of component (a) is particularly a lubricating oil or grease wherein the base medium is a hydrocarbon or synthetic lubricant. The preferred base fluids of this invention include the hydrocarbon mineral oils, olefin fluids, polyolefin fluids, polyether fluids, polyacetals, alkylene oxide polymers, silicone-base fluids and ester fluids. The esters of dicarboxylic acids and monohydric alcohols and the trimethylolpropane and pentaerythritol esters of monocarboxylic acids are particularly of interest. Suitable diesters include the esters of oxalic, malonic, succinic, glutaric, adipic, pimelic, suberic, azelaic and sebacic acids, cyclohexane dicarboxylic acid, phthalic acid, terephthalic acid and the like; and alcohols having 1 to 20 carbon atoms. A commonly used diester is di(2-ethylhexyl) sebacate.

The acids used in forming the trimethylolpropane and pentaerythritol esters include those containing 1 to 30 carbon atoms having straight or branched chain aliphatic, cycloaliphatic, aromatic or alkylated aromatic structures. Mixtures of one or more of such acids may also be used in the preparation of these tri- and tetra-esters. Typical carboxylic acids include, acetic, propionic, butyric, valeric, isovaleric, caproic, caprylic, pelargonic, capric, isodecanoic, lauric, benzoic, nonylbenzoic, dodecylbenzoic, naphthoic, cyclohexanoic and the like. The acids most particularly preferred are pelargonic and commeric valeric acid which contains both n-valeric and isovaleric acids.

The most preferred ester used in this invention is an ester prepared from pentaerythritol, pelargonic, n-valeric and isovaleric acids.

The instant compounds are sufficiently soluble in lubricants to afford the desired antioxidant stabilizing effects. Suitable concentrations range from about 0.001% to about 10% by weight based on the total lubricant composition. Preferably the effective stabilizing amount of the instant compounds is from about 0.1% to about 5% by weight of the total lubricant composition.

The lubricant composition of the instant invention find a wide variety of end uses including engine oils, such as aviation engine oils, automotive engine oils, diesel engine oils, railroad diesel oils, truck diesel oils and the like.

The lubricating oil may be a mineral oil, a synthetic oil or any mixture of such oils. Mineral oils are preferred and examples of these include paraffinic hydrocarbon oils e.g. a mineral oil having a viscosity of 46 $mm^2/s$ at 40° C.; "150 Solvent Neutral" a solvent refined neutral mineral oil having a viscosity of 32 $mm^2/s$ at 40° C.; and "solvent bright-stocks", a high boiling residue from the process of refining mineral oil, and having a viscosity of 46 $mm^2/s$ at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: $G_1$—$OCC$-alkylene-$COOG_2$ wherein "alkylene" denotes an alkylene residue having from 2 to 14 carbon atoms and $G_1$ and $G_2$ are the same or different and each is an alkyl group having from 6 to 18 carbon atoms. Tri-esters which are of use as lubricating oil base stocks are those derived from trimethylolpropane and $C_6$–$C_{18}$ mono-carboxylic acids or mixtures thereof, whereas suitable tetra-esters include those derived from pentaerythritol and a $C_6$–$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

Examples of phenolic antioxidants

1. Alkylated Monophenols: 2,6-Di-tert-butyl-4-methylphenol, 2,6-di-tert-butylphenol, 2-tert-butyl-4,6-dimethylphenol, 2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol, o-tert-butylphenol.

2. Alkylated Hydroquinones: 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers: 2,2'-Thio-bis-(6-tert-butyl-4-methylphenol), 2,2'-thio-bis-(4-octylphenyl), 4,4'-thio-bis-(6-tert-butyl-3-methylphenol), 4,4'-thio-bis-(6-tert-butyl-2-methylphenol).

4. Alkylidene-Bisphenols: 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or 5-isobutylphenol), 2,2'-methylene-bis-(6-(α-methylbenzyl-4-nonylphenol), 2,2'-methylene-bis-(6-(α,α-dimethylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methyl-phenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate],bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds: 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiol-terephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols: 4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, trihydroxyethyl isocyanurate, thiodiethylene glycol, bis-hydroxyethyl-oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants: N,N'-Di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethylbutyl)-N'-phenyl-p-phenylenediamine, N-(1-methyl-heptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diaminodiphenyl-methane, N,N,N',N'-tetramethyl-4,4'-diamino-diphenylmethane, 1,2-di-(phenyl-amino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allyl-phenothiazine, tert-octylated phenothiazine, 3,7-di-tert-octylphenothiazine.

Examples for other antioxidants: Aliphatic or aromatic phosphites, esters of thiodipropionic acid or of thiodiacetic acid, or salts of dithiocarbamic or dithiophosphoric acid.

Examples of metal passivators, for example for copper, are: Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

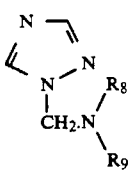

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are:

a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

b) Nitrogen-containing compounds, e.g.

I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonylnaphthalene-n-sulfonates, calcium petroleum sulfonates.

e) Derivatives of gamma-alkoxypropylamines described in Japanese Patent Publication No. 15783/1973; and f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 3437 876 (German Offenlegungsschrift).

g) Compounds having the formula

$R_{12}-X_2-CH_2-CH(OH)-CH_2NR_{13}R_{14}$ in which $X_2$ is $-O-$, $-S-$, $-SO_2-C(O)-O-$ or $-N(Rd)$ in which $R_{12}$ is H or $C_1-C_{12}$alkyl, $R_{13}$ is unsubstituted $C_1-C_4$alkyl or $C_2-C_5$alkyl substituted by one to three hydroxyl groups, $R_{14}$ is hydrogen, unsubstituted $C_1-C_4$alkyl or $C_2-C_5$alkyl substituted by one to three hydroxyl groups provided that at least one of $R_{13}$ and $R_{14}$ is hydroxy-substituted, and $R_{12}$ is $C_2-C_{20}$alkyl $-CH_2-CH(OH)-CH_2NR_{13}R_{14}$ or $R_{12}$ is $C_2-C_{18}$alkenyl, $C_2-C_3$alkynyl or $C_5-C_{12}$cycloalkyl provided that, when $X_2$ is $-O-$ or $-C(O)-O-$, $R_{12}$ is branched $C_4-C_{20}$alkyl. These compounds are described in GB Patent Specification 2172284A.

h) Compounds having the formula:

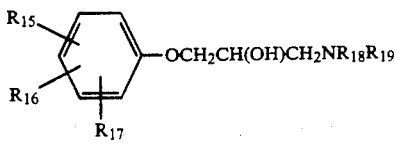

in which $R_{15}$, $R_{16}$, $R_{17}$ are, independently, hydrogen, $C_1-C_{15}$alkyl, $C_5-C_{12}$cycloalkyl, $C_6-C_{15}$aryl or $C_7-C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each $-CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are: Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of pour-point depressants are: Polymethacrylates, alkylated naphthalene derivatives.

Examples of dispersants/detergents are: Polybutenylsuccinic acid-amides or -imides, polybutenyl-phosphonic acid derivatives, basic magnesium-, calcium-, and bariumsulfonates and -phenolates.

Examples of anti-wear additives and extreme pressure additives are: Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The following examples are presented for the purpose of illustration only and are not to be construed as limiting the nature or scope of the instant invention in any manner whatsoever.

EXAMPLE 1

N-Allyl-1,8-naphthalenediamine

In a 100 ml three-necked flask equipped with a stirrer, thermometer, condenser, dropping funnel and nitrogen inlet is placed 100 ml of a 50% aqueous sodium hydroxide solution. A solution of 15.8 g (0.1 m) of 1,8-naphthalenediamien dissolved in 50 ml of methylene chloride is added to the stirred alkali solution followed by 3.4 g (0.01 m) of tetrabutyl ammonium hydrogen sulfate. A solution of 12.1 g (0.1 m) of allyl bromide dissolved in 50 ml of methylene chloride is placed in the dropping funnel and then added dropwise to the reaction mixture at room temperature. A deep red color develops. The reaction mixture is stirred at room temperature for 24 hours and then transferred to a separatory funnel with toluene. The organic layer is separated, washed free of alkali with water and then dried over anhydrous sodium sulfate. The solvent is removed under reduced pressure and the crude residue purified by flash chromatography using silica gel. The title compound is obtained in a yield of 5.9 g as a brown oil.

$^1$H NMR and $^{13}$C NMR spectra obtained are consistent with the structure of the title compound.

Analysis: Calcd for $C_{13}H_{14}N_2$: C, 78.5; H, 7.1; N, 14.1. Found: C, 79.0; H, 6.8; N, 15.0.

EXAMPLES 2-5

When using the general procedure of Example 1 the molar amount of allyl bromide to 1,8-naphthalenediamine is increased from 1:1 to 1:2 to 1:5, increasing amounts of allyl substitution on the N-atoms of 1,8-naphthalenediamine is obtained as is shown in the table below.

| Example | Product* |
|---|---|
| 2 | mixture of N,N-diallyl and N,N'-diallyl-1,8-naphthalenediamine |
| 3 | mixture of N-allyl-,N,N'-diallyl-,N,N-diallyl-,N,N,N'-triallyl- and N,N,N',N'-tetraallyl-1,8-naphthalenediamine |
| 4 | mixture like that of Example 4 |
| 5 | N,N,N',N'-tetraallyl-1,8-naphthalenediamine |

*in each example the product is a brown oil

The mixture of products in each of these examples can be conveniently separated into their component parts using conventional flash chromatography methods.

EXAMPLE 6

N,N,N',N'-Tetramethallyl-1,8-naphthalenediamine

When using the general procedure of Example 1 and at least a 5 to 1 molar ratio of methallyl chloride to 1,8-naphthalenediamine, the title compound is obtained. Analogously, by varying the ratio of methallyl halide to diamine, the composition of the product obtained varies to encompass examples in which the predominant species are the mono-, di- or tri-methallylated derivatives.

The individual components can be separated conveniently using convention flash chromatography methods.

EXAMPLES 7-9

When the general procedure of Example 1 is followed, but substituting 1,5-naphthalenediamine for 1,8-naphthalenediamine, and using a four molar ratio of allyl bromide to naphthalenediamine, the following products are obtained as brown oils. The compounds are readily separable by chromatography.

| Example | Product |
|---|---|
| 7 | mixture of N-allyl-,N,N-diallyl-, N,N'-diallyl-,N,N,N'-triallyl-, and N,N,N',N'-tetraallyl-1,5-naphthalenediamine |
| 8* | N,N,N',N'-tetraallyl-1,5-naphthalenediamine |
| 9** | N,N,N'-triallyl-1,5-naphthalenediamine |

*Analysis:
Calcd for $C_{22}H_{26}N_2$: C, 83.0; H, 8.2; N, 8.8.
Found: C, 82.5; H, 8.5; N, 8.5.
**Analysis:
Calcd for $C_{19}H_{22}N_2$: C, 82.0; H, 8.0; N, 10.0.
Found: C, 82.1; H, 8.1; N, 9.8.

EXAMPLE 10

N,N,N',N'-Tetra(n-octylthiomethyl)-1,5-naphthalenediamine

To a flask fitted with a stirrer, thermometer, condenser and nitrogen inlet are added 1,5-naphthalenediamine, n-octyl mercaptan, 37% aqueous formaldehyde and methanol solvent. A four molar plus 10% excess of 1,5-naphthalenediamine to n-octyl mercaptan is used. The reaction mixture is heated to reflux for six hours and then allowed to cool to room temperature with stirring overnight. The reaction mixture is then extracted with diethyl ether and the organic layer is separated and dried over anhydrous sodium sulfate. The solvent is removed under reduced pressure and the crude residue is purified by flash chromatography using silica gel. The fraction containing the desired compound is recrystallized from petroleum ether to give the title compound.

Analysis: Calcd for $C_{46}H_{82}N_2S_4$: C, 69.8; H, 10.5; N, 3.5; S, 16.2. Found: C, 69.2; H, 11.0; N, 3.2; S, 16.0.

EXAMPLE 11

N,N,N',N'-Tetra[2-(n-octylthio)ethylthiomethyl]-1,5-naphthalenediamine

Following the general method of Example 10, the title compound is obtained by the reaction of 1,5-naphthalenediamine, 2-(n-octylthio)ethylmercaptan and 37% aqueous formaldehyde.

In an analogous manner, by varying the molar ratios of mercaptan to diamine, composition of the product mixtures may be varied to encompass examples in which the predominant species are the mono-, di- or tri-substituted thiomethyl derivatives.

The individual compounds can be conveniently separated using conventional flash chromatography methods.

EXAMPLE 12

The instant compounds are tested for their antioxidant activity in lubricant compositions using the Thin-Film Oxygen Uptake Test Thin-Film Oxygen Uptake Test (TFOUT) method according to ASTM D4742.

The instant compounds are added at the 0.5% by weight concentration into a standard crankcase formulation (API 1119) whose performance in TFOUT testing is known to correlate well with ultimate engine performance. The longer the time indicated for antioxidant activity indicates a more efficacious stabilizer. The results of these tests are given in the table below.

| 0.5% by weight of Compound of Example | TFOUT Time (minutes) |
|---|---|
| None | 110 |
| 1 | 214 |
| 3 | 209 |
| 4 | 145 |
| 5 | 184 |
| 7 | 197 |
| 8 | 211 |
| 9 | 181 |

Each of the instant compounds show significant antioxidant activity in this standard lubricant composition.

What is claimed is:

1. An N-substituted 1,5- or 1,8-naphthalenediamine of formula I or II

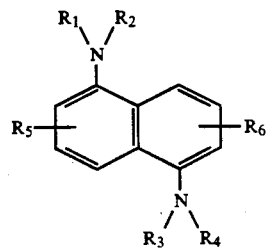

(I)

-continued

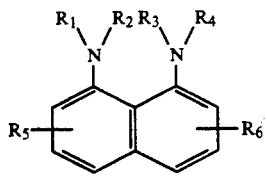

wherein

R$_1$, R$_2$, R$_3$ and R$_4$ are independently hydrogen, alkenyl of 3 to 18 carbon atoms or —CH$_2$—S—E$_1$ or —CH$_2$—S—C$_n$H$_{2n}$—S—E$_1$ where n is 2 to 6, E$_1$ is alkyl of 1 to 18 carbon atoms, alkenyl of 3 to 18 carbon atoms, cycloalkyl of 5 to 12 carbon atoms, phenylalkyl of 7 to 9 carbon atoms, aryl of 6 to 10 carbon atoms, or said aryl or said phenylalkyl substituted on the aryl or phenyl moiety by one or two alkyl of 1 to 8 carbon atoms or by hydroxy and by one or two alkyl of 1 to 8 carbon atoms, with the proviso that all of R$_1$, R$_2$, R$_3$ and R$_4$ are not hydrogen at the same time, and with the further proviso that in formula II, none of R$_1$, R$_2$, R$_3$ and R$_4$ is —CH$_2$S—E$_1$ or —CH$_2$—S—C$_n$H$_{2n}$—S—E$_1$ or, and R$_5$ and R$_6$ are independently hydrogen, alkyl of 1 to 12 carbon atoms, alkenyl of 3 to 18 carbon atoms, cycloalkyl of 5 to 12 carbon atoms, phenylalkyl of 7 to 15 carbon atoms or aryl of 6 to 10 carbon atoms.

2. A compound according to claim 1 wherein R$_1$, R$_2$, R$_3$ and R$_4$ are independently hydrogen, allyl, methallyl, —CH$_2$—S—E$_1$ or —CH$_2$—S—C$_n$H$_{2n}$—S—E$_1$ or where n is 2, E$_1$ is alkyl of 2 to 12 carbon atoms, with the proviso that at least two of R$_1$, R$_2$, R$_3$ and R$_4$ are not hydrogen.

3. A compound according to claim 2 wherein R$_1$, R$_2$, R$_3$ and R$_4$ are independently hydrogen, allyl, methallyl, or —CH$_2$—S—E$_1$ or where E$_1$ is alkyl of 8 to 12 carbon atoms, and at least two of R$_1$, R$_2$, R$_3$ and R$_4$ are not hydrogen.

4. A compound according to claim 3 wherein at least one of R$_1$, R$_2$, R$_3$ and R$_4$ is allyl.

5. A compound according to claim 1 wherein R$_5$ and R$_6$ are independently hydrogen or alkyl of 1 to 4 carbon atoms.

6. A compound according to claim 5 wherein R$_5$ and R$_6$ are each hydrogen.

7. The compound according to claim 1 which is N-allyl-1,8-naphthalenediamine.

8. The compound according to claim 1 which is N,N,N',N'-tetraallyl-1,8-naphthalenediamine.

9. The compound according to claim 1 which is N,N,N'-triallyl-1,5-naphthalenediamine.

10. The compound according to claim 1 which is N,N,N',N'-tetraallyl-1,5-naphthalenediamine.

11. A compound according to claim 1 which is selected from the group consisting of
N,N,-diallyl-1,8-naphthalenediamine;
N,N'-diallyl-1,8-naphthalenediamine;
N,N,N'-triallyl-1,8-naphthalenediamine;
N-allyl-1,5-naphthalenediamine;
N,N-diallyl-1,5-naphthalenediamine;
N,N'-diallyl-1,5-naphthalenediamine;
N,N,N',N'-tetra(n-octylthiomethyl)-1,5-naphthalenediamine;
N,N,N',N'-tetra(methallyl)-1,8-naphthalenediamine; and
N,N,N',N'-tetra[2-(n-octylthio)ethylthiomethyl]-1,5-naphthalenediamine.

12. A lubricant composition, having improved oxidation or thermal stability, which comprises
(a) a major amount of a lubricant, subject to oxidative or thermal degradation, and
(b) an effective stabilizing amount of a compound of formula I or II according to claim 1.

13. A composition according to claim 12 wherein the compound of component (b) is N-allyl-1,8-naphthalenediamine.

14. A composition according to claim 12 wherein the compound of component (b) is N,N,N',N'-tetraallyl-1,5-naphthalenediamine.

15. A composition according to claim 12 wherein the compound of component (b) is selected from the group consisting of
N,N,N',N'-tetraallyl-1,8-naphthalenediamine;
N,N,N'-triallyl-1,5-naphthalenediamine;
N,N,-diallyl-1,8-naphthalenediamine;
N,N'-diallyl-1,8-naphthalenediamine;
N,N,N'-triallyl-1,8-naphthalenediamine;
N-allyl-1,5-naphthalenediamine;
N,N-diallyl-1,5-naphthalenediamine;
N,N'-diallyl-1,5-naphthalenediamine;
N,N,N',N'-tetra(n-octylthiomethyl)-1,5-naphthalenediamine;
N,N,N',N'-tetra(methallyl)-1,8-naphthalenediamine; and
N,N,N',N'-tetra[2-(n-octylthio)ethylthiomethyl]-1,5-naphthalenediamine.

* * * * *